(12) United States Patent
Cahan et al.

(10) Patent No.: US 10,828,139 B2
(45) Date of Patent: Nov. 10, 2020

(54) AUTOMATED INTRA-ORAL THERAPEUTIC DELIVERY

(71) Applicant: INTERNATIONAL BUSINESS MACHINES CORPORATION, Armonk, NY (US)

(72) Inventors: Amos Cahan, Dobbs Ferry, NY (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 79 days.

(21) Appl. No.: 15/814,446

(22) Filed: Nov. 16, 2017

(65) Prior Publication Data

US 2018/0360582 A1 Dec. 20, 2018

Related U.S. Application Data

(63) Continuation of application No. 15/626,484, filed on Jun. 19, 2017.

(51) Int. Cl.
| | | |
|---|---|---|
| *A61C 19/06* | (2006.01) | |
| *A61K 8/02* | (2006.01) | |
| *A61Q 11/00* | (2006.01) | |
| *A61C 19/00* | (2006.01) | |
| *A61F 5/00* | (2006.01) | |

(52) U.S. Cl.
CPC ........ *A61C 19/063* (2013.01); *A61C 19/06* (2013.01); *A61K 8/02* (2013.01); *A61Q 11/00* (2013.01); *A61C 19/00* (2013.01); *A61F 5/00* (2013.01)

(58) Field of Classification Search
CPC ....... A61C 19/06; A61C 19/063; A61C 19/00; A61M 31/002; A61F 5/00
See application file for complete search history.

(56) References Cited

U.S. PATENT DOCUMENTS

| | | |
|---|---|---|
| 5,433,952 A | 7/1995 | Sipos |
| 7,766,658 B2 | 8/2010 | Tricca et al. |
| 8,715,269 B2 | 5/2014 | Wolff et al. |
| 9,462,822 B2 | 10/2016 | Baym et al. |
| 2004/0158194 A1 | 8/2004 | Wolff et al. |
| 2006/0166157 A1* | 7/2006 | Rahman ............... A61B 5/4833 433/6 |
| 2007/0016163 A1 | 1/2007 | Santini, Jr. et al. |
| 2010/0324382 A1 | 12/2010 | Cantwell et al. |
| 2014/0121594 A1* | 5/2014 | Connor ................. A61F 5/0006 604/77 |

(Continued)

OTHER PUBLICATIONS

Amos Cahan et al., "Automated Intra-Oral Therapeutic Delivery", Related Application, U.S. Appl. No. 15/626,484, filed Jun. 19, 2017.

(Continued)

*Primary Examiner* — Rebecca E Eisenberg
*Assistant Examiner* — Anh Bui
(74) *Attorney, Agent, or Firm* — Cantor Colburn LLP

(57) ABSTRACT

Embodiments of the present invention are directed to a system for automated intra-oral delivery of therapeutic agents. A non-limiting example of the system includes a delivery vessel including a control unit and a reservoir. The system can also include a connector tube including a channel coupled to the delivery vessel. The system can also include a sensor coupled to connector tube.

7 Claims, 11 Drawing Sheets

(56) References Cited

U.S. PATENT DOCUMENTS

| | | |
|---|---|---|
| 2015/0343208 A1 | 12/2015 | Davidovitch et al. |
| 2016/0278899 A1 | 9/2016 | Heller et al. |
| 2017/0172961 A1* | 6/2017 | Heller .................. A61K 31/195 |
| 2018/0132968 A1* | 5/2018 | Miller .................. A61C 17/005 |
| 2018/0263540 A1 | 9/2018 | Zafar et al. |

OTHER PUBLICATIONS

List of IBM Patents or Patent Applications Treated as Related; (Appendix P), Filed Nov. 16, 2017; pp. 1-2.

Zafar et al., "A comparison between bipolar transistor and nanowire field effect transistor biosensors," Applied Physics Letters, vol. 106, No. 6, 2015, 063701, 4 pages.

Zafar et al., "Bipolar junction transistor based sensors for chemical and biological sensing." 46th European Solid-State Device Research Conference, 2016, pp. 389-392.

* cited by examiner

AUTOMATED INTRA-ORAL THERAPEUTIC DELIVERY

DOMESTIC AND/OR FOREIGN PRIORITY

This application is a continuation of U.S. application Ser. No. 15/626,484, titled "Automated Intra-Oral Therapeutic Delivery" filed Jun. 19, 2017, the contents of which are incorporated by reference herein in its entirety.

BACKGROUND

The present invention generally relates to medical devices and related methods, and more specifically to automated intra-oral therapeutic delivery and related methodologies.

Within the oral cavity, an acidic environment can promote demineralization of tooth enamel. Such demineralization can lead to tooth erosions and dental cavities, or caries. Sugar fermentation by the oral microbiome, such as in dental plaque, can acidify the intra-oral environment. Saliva can act as a buffer and neutralize intra-oral pH. Moreover, saliva has a high concentration of calcium and phosphate, which can decrease demineralization and promote remineralization of tooth enamel. When the balance between demineralization and remineralization changes, caries can progress and cause breakdown of the enamel surface. Several medical conditions are associated with decreased intra-oral saliva content and the evolvement of an acidic environment and, thus, have potential to increase tooth erosions and dental caries.

SUMMARY

Embodiments of the present invention are directed to a system for automated intra-oral delivery of therapeutic agents. A non-limiting example of the system includes a delivery vessel including a control unit and a reservoir. The system can also include a connector tube including a channel coupled to the delivery vessel. The system can also include a sensor coupled to connector tube.

Embodiments of the present invention are directed to a method for maintaining oral cavity health. A non-limiting example of the method includes sensing, by a sensor positioned within the oral cavity of a patient, an oral cavity condition. The method can also include determining, by a control unit in communication with the sensor and a pump, whether to deliver a therapeutic agent to the oral cavity. The method can also include activating, by the control unit, the pump to deliver the therapeutic agent to the oral cavity.

Embodiments of the present invention are directed to a method for intra-oral therapeutic delivery. A non-limiting example of the method includes affixing a delivery vessel including a control unit, a reservoir including a therapeutic agent, and an adhesive backing to a patient. The method can also include positioning a connector tube in communication with the reservoir in an oral cavity of the patient, wherein the connector tube includes a sensor. The method can also include sensing a condition of the oral cavity of the patient with the sensor. The method can also include, based upon the sensed condition, delivering the therapeutic agent to the oral cavity of the patient.

Embodiments of the present invention are directed to an apparatus for automated intra-oral therapeutic delivery. A non-limiting example of the apparatus includes a pH sensor including a reference electrode and a plurality of field effect transistor (FET) devices, wherein each of the plurality of FET devices includes a gate dielectric including a FET sensing surface, a source, a drain, and a substrate. The apparatus also includes automation circuitry including a processing unit in communication with the pH sensor and a pump. The apparatus also includes a reservoir in communication with the pump. The apparatus also includes a connector tube including a passage from the reservoir to a distal opening, wherein the distal opening is capable of being positioned in an oral cavity of a patient.

Embodiments of the present invention are directed to an apparatus for automated intra-oral therapeutic delivery. A non-limiting example of the apparatus includes a pH sensor including a reference electrode and a plurality of sensing surfaces, wherein each of the plurality of sensing surfaces is connected to a base of a bipolar junction transmitter (BJT) device, wherein the BJT-device further includes a collector and an emitter. The apparatus also includes automation circuitry including a processing unit in communication with the pH sensor and a pump. The apparatus also includes a reservoir in communication with the pump. The apparatus also includes a connector tube including a passage from the reservoir to a distal opening, wherein the distal opening is capable of being positioned in an oral cavity of a patient.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
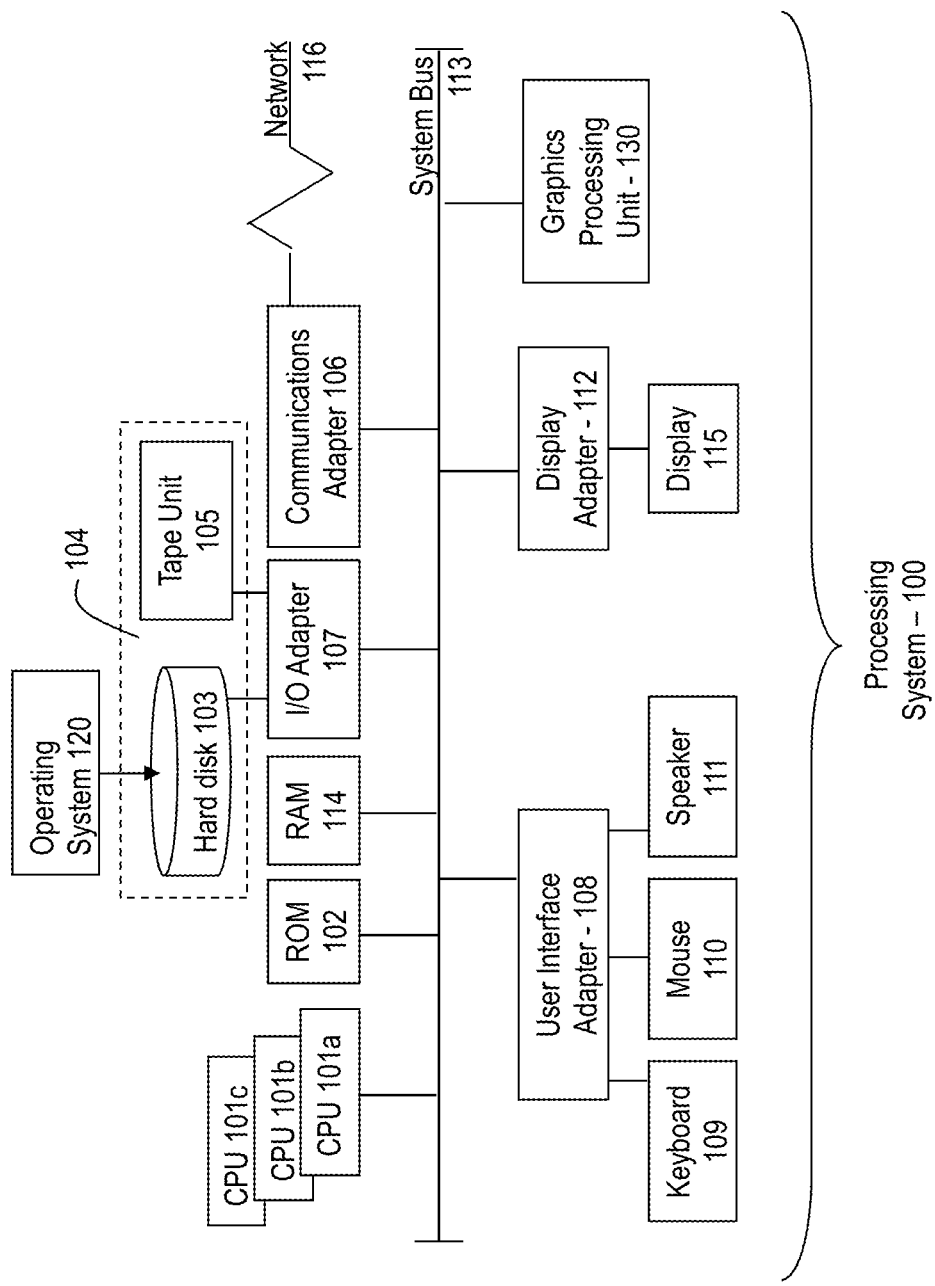
FIG. 1 depicts a block diagram illustrating one example of a processing system according to one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can include any integer number greater than or equal to one, i.e. one, two, three, four, etc. The terms "a plurality" can include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Additionally, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Spatially relative terms, e.g., "beneath," "below," "lower," "above," "upper," and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device can be otherwise oriented (rotated 90 degrees or at other orientations) and the spatially relative descriptors used herein interpreted accordingly.

Turning now to an overview of technologies that are more specifically relevant to aspects of the invention, an acidic intra-oral environment (pH less than about 5.5) can adversely impact dental health by promoting enamel demineralization. The oral microbiome, predominantly in dental plaque, can acidify the intra-oral environment through sugar fermentation. Moreover, a number of physiological conditions can promote an acidic intra-oral environment, in some cases through decreased intra-oral saliva content.

Saliva can promote oral health by neutralizing intra-oral pH through a buffering action and by decreasing demineralization and increasing remineralization by providing calcium and phosphate to the intra-oral cavity. When the balance between demineralization and remineralization changes, caries can progress and cause breakdown of tooth enamel.

Several conditions are associated with decreased intra-oral saliva content and the evolution of an acidic environment. For example, even in otherwise healthy individuals, saliva secretion is reduced during sleep. Moreover, breathing through the mouth during sleep can increase saliva evaporation and has been associated with intra-oral pH levels of less than 4, shifting the equilibrium toward demineralization. Dry mouth, or xerostomia, carries with it an increased risk of dental caries. Xerostomia can accompany inflammatory diseases (e.g., Sjogren's syndrome) and is often a result of adverse drug effects. In addition, persons mechanically ventilated with an orotracheal tube are unable to fully close their mouth and can develop xerostomia. Such ventilated individuals and in other debilitated patients can further experience decreased oral hygiene accompanied by increased bacterial growth. Not only can dental caries result, but also other infectious processes such as gingivitis and abscesses. Another common problem that can be aggravated by xerostomia and bacterial overgrowth is halitosis, or bad breath. Halitosis can be worse after sleep due, for example, to reduced saliva secretion and saliva evaporation.

There is a need to maintain a non-acidic environment in the oral cavity, including during sleep. There is also a need to alleviate halitosis caused or exacerbated by dry mouth and an acidic intra-oral environment during sleep.

The oral cavity can be affected by other pathologies and inflammatory processes that can cause health risks and patient discomfort. For instance, Oropharyngeal candidiasis ("thrush"), a fungal infection, can cause significant oral discomfort and can affect immunosuppressed individuals, diabetics, and persons receiving antibiotics. Thrush is also promoted by xerostomia. In addition to fungal infections, viral infections including, such as Herpes Simplex and associated mouth ulcers, and conditions such as aphthous stomatitis, which causes recurrent ulcers, can also cause oral pain and discomfort and can interfere with eating. Topical treatments used to treat such conditions can have short half-life and, thus, require frequent reapplication for optimal efficacy. Such frequent reapplication is not only burdensome on patients and caregivers, but also impractical during sleep.

There remains a need to provide efficient, around the clock treatment for patients with such conditions.

Turning now to an overview of the aspects of the invention, one or more embodiments of the invention provide an automated delivery system including a sensor, a control unit and a reservoir for providing therapeutic agents to an oral cavity. Some embodiments of the invention provide a system that can easily be affixed to a patient, such as on a cheek or on a tooth, and can provide automated delivery to an oral cavity according to a pre-determined schedule or to a schedule dependent upon data derived from one or more sensors in the oral cavity. Some embodiments of the invention provide real-time and/or sensitive measurements of conditions in the oral cavity, such as pH, humidity, or ionic composition of local fluids, and can deliver therapeutic agents based upon such conditions.

The above-described aspects of the invention can meet such needs by providing automated intra-oral administration of substances that can promote oral health by maintaining intra-oral physiologic conditions or by administering topical therapeutics. Embodiments of the invention can maintain a non-acidic environment in the oral cavity, including during sleep. Some embodiments of the invention can alleviate halitosis during sleep. Some embodiments of the invention can provide efficient, non-cumbersome, around the clock treatment for conditions affecting the oral cavity.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 1 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

In exemplary embodiments of the invention, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2A:
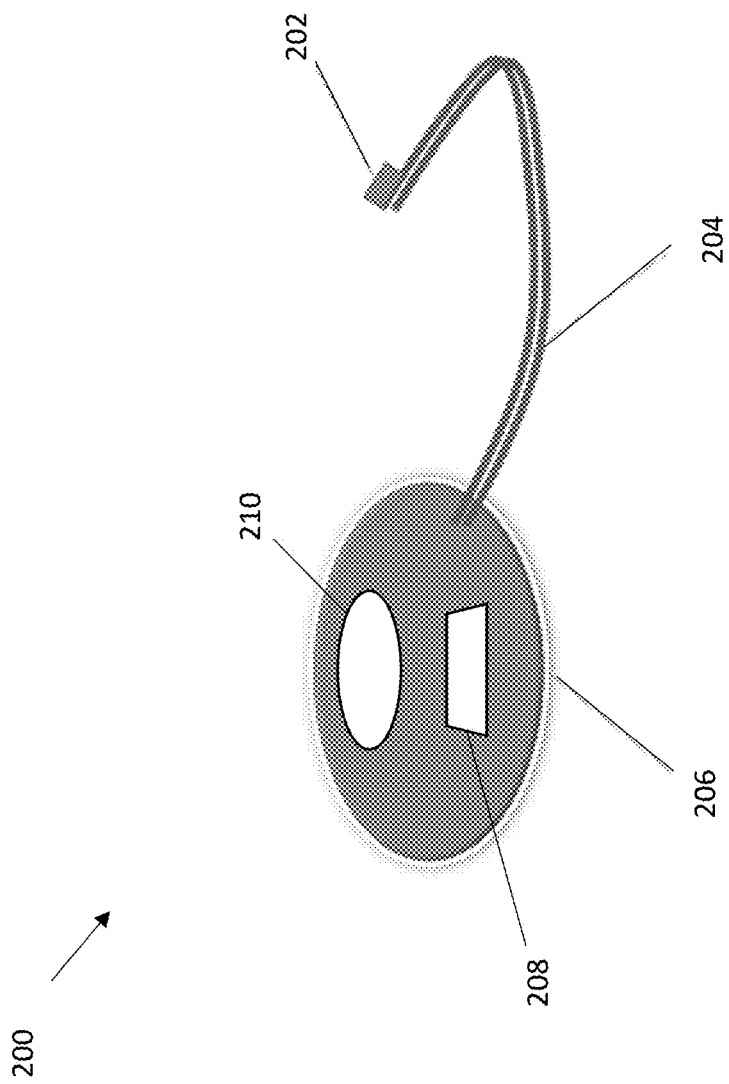
FIG. 2A depicts an exemplary system according to one or more embodiments of the present invention.

Turning now to a more detailed description of aspects of the present invention, FIG. 2A depicts an automated intra-oral delivery system 200 according to embodiments of the invention. The system 200 can include one or more sensors 202 connected to the connector tube 204. The delivery vessel 206 can include a control unit 208 and a reservoir 210. The connector tube 204 can include a passage from the delivery vessel to a distal opening sized to be positioned within an oral cavity of a human.

Sensors 202 can include any sensor useful for determining a condition of the intra-oral cavity useful for promotion of health. In some embodiments of the invention, a sensor 202 includes a pH sensor, a wetness sensor, a humidity sensor, a flow sensor, a chemical or ion sensor, such as a calcium, potassium, or phosphorous sensor, and/or an organic molecule sensor, such as a nucleic acid sensor. In some embodiments of the invention the sensor is a sensor selected from the group consisting of a pH sensor, a humidity sensor, a calcium sensor, a potassium sensor, and an organic molecule sensor.

In some embodiments of the invention, the sensor 202 includes a sensor selective for specific ions. Sensors including ion specific electrodes are known and include, for example, glass membranes, crystalline membranes, and electrodes specific for certain ions, including solid-state electrodes including insoluble inorganic materials, such as silver sulfide, copper sulfide, cadmium sulfide, lead sulfide, lanthanum fluoride, silver chloride, silver iodide, and silver thiocyanate. Ion selectivity can be modulated by changes in a sensing surface, for example by selectively using a silver surface over a titanium nitride surface.

In some embodiments of the invention, the sensor 202 is covered by a protective membrane, such as a protective semi-permeable membrane that can prevent accumulation of debris (e.g., cells or food stuff) on the sensing area.

In some embodiments of the invention, the sensor 202 includes a pH sensor. In some embodiments of the invention, the pH sensor is a bipolar junction transmitter (BJT)-based pH sensor. In some embodiments of the invention, the pH sensor is a field effect transmitter (FET)-based pH sensor.

The sensor 202 can include an intrinsic or extrinsic power supply. In some embodiments of the invention, the sensor 202 is in communication with a power supply located on the delivery vessel 206. For example, a power supply on the reservoir 210 or in the control unit 208 can supply power to the sensor 202.

The delivery vessel 206 can include one or more reservoirs 210. The reservoir 210 can be any shape or size practical for administration and storage of a therapeutic substance. In some embodiments of the invention, the reservoir 210 includes a therapeutic substance or agent. Therapeutic substances or agents that can be included in the reservoir 210 include, but are not limited to, one or more of pH adjusting agents, such as sodium bicarbonate, oral treatment agents, such as fluoride, chlorhexidine, artificial saliva, topical antifungal agents or preparations, such as fluconazole, nystatin, acyclovir, local anesthetics, such as lidocaine, lubricants, plant extracts, breath fresheners, topical cholinergic or anticholinergic agents, and solutions and mixtures thereof. In some embodiments of the invention, at least two reservoirs are included in a delivery vessel 206, wherein a first reservoir includes a therapeutic agent and a second reservoir includes a solvent. Solvents can include any biocompatible solutions for dissolution or dilution of one or more therapeutic substances, such as, for example, water, saline, or dextrose.

Control unit 208 can include a microprocessor. The microprocessor, for example, can be capable of controlling the release of therapeutic substances. In some embodiments of the invention, the control unit 208 provides release of therapeutic substances according to a pre-programmed schedule. In some embodiments of the invention, the control unit 208 provides release of therapeutic substances based upon an analysis of signals received from the sensor(s) 202. Therapeutic substances can be released from the reservoir 210 and carried through the connector tube 204 and released to the oral cavity at a distal end of the connector tube 204. The connector tube 204, for instance, can include a polymeric material and can be flexible in whole or part.

Figure 2B:
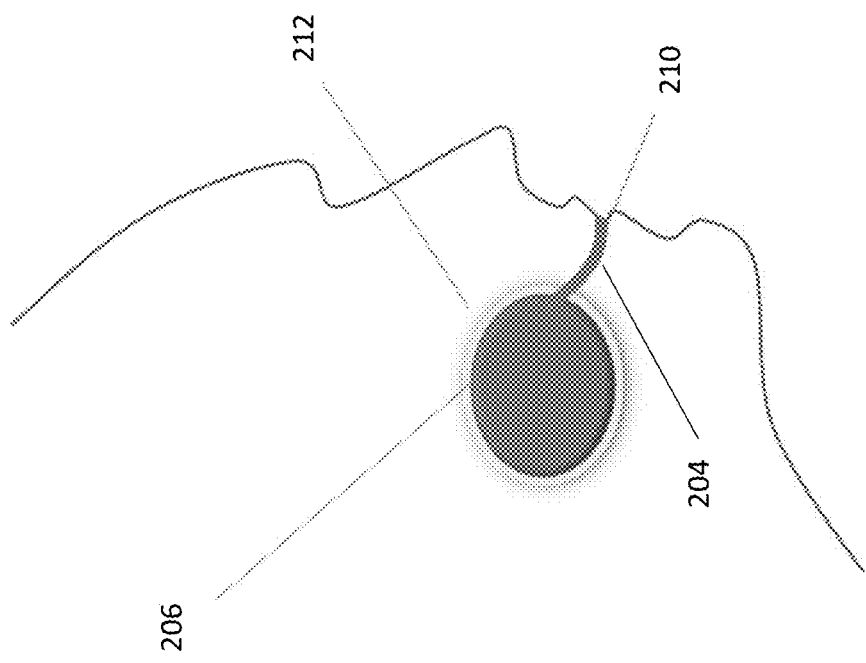
FIG. 2B depicts an exemplary system positioned on a user according to one or more embodiments of the present invention.

FIG. 2B illustrates an exemplary automated intra-oral delivery system coupled to a user. The exemplary system can include a delivery vessel 206 coupled to the outside of the user's face 212, for instance on a cheek. The connector tube 204 can include a channel for delivery of therapeutic substances into the mouth 210. In some embodiments of the invention (not shown in FIG. 2B), the delivery vessel 206 is positioned inside the oral cavity of a user, for instance on an inner wall of the cheek or by affixing the delivery vessel to a tooth. The delivery vessel 206 can include an adhesive backing in some embodiments of the invention for adherence to a surface of the user.

Figure 3:
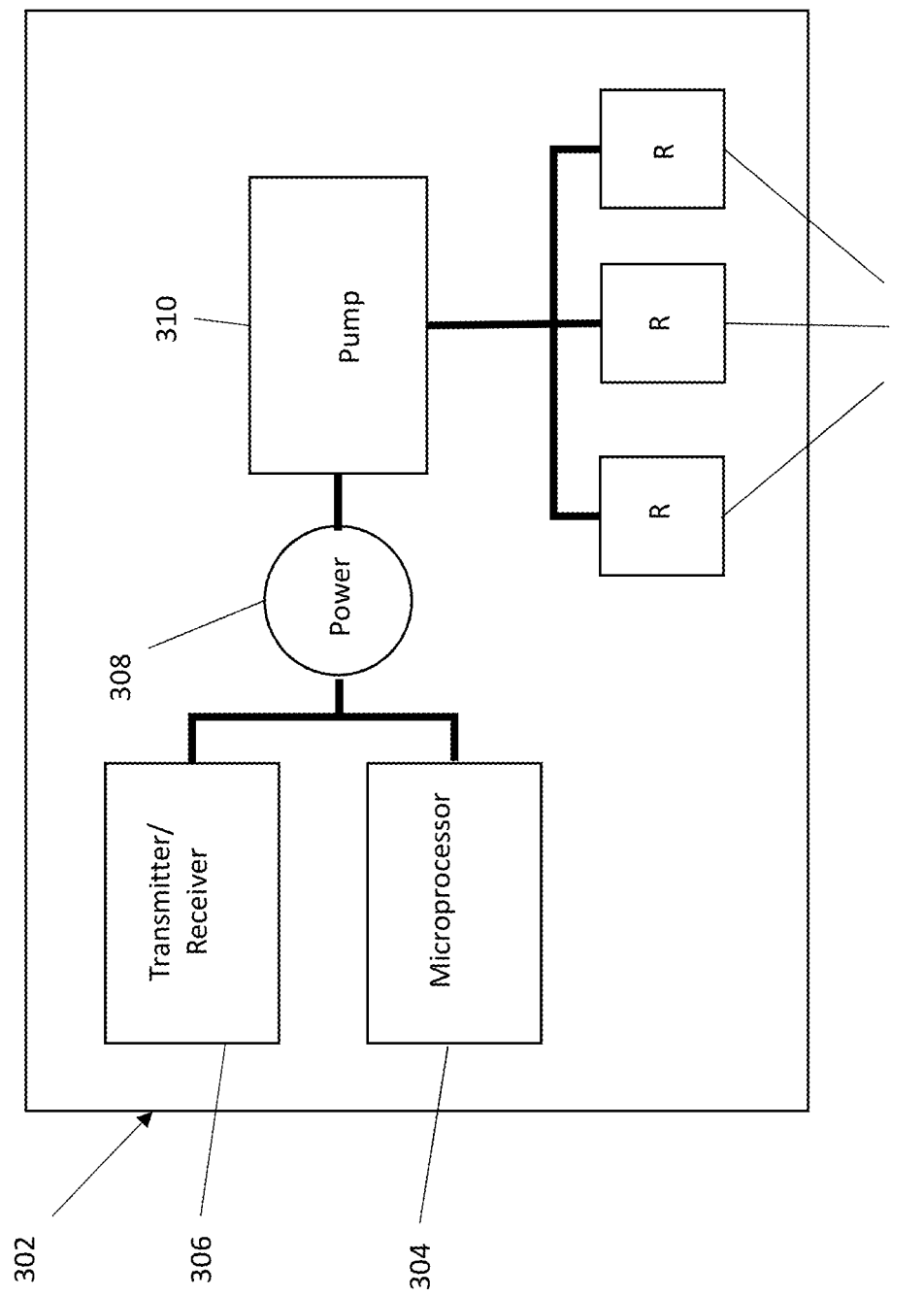
FIG. 3 depicts an exemplary system according to one or more embodiments of the present invention.

FIG. 3 depicts a schematic of an exemplary delivery vessel 302 in accordance with one or more embodiments of the invention. The delivery vessel 302 includes a microprocessor 304 in communication with a power supply 308 and a pump 310. The pump 310 can communicate with one or more reservoirs 312, which can store an amount of liquid, gel, or solid therapeutic substances. In some embodiments of the invention a solid therapeutic substance included within a reservoir is packaged in granules. In some embodiments of the invention, the delivery vessel includes a transmitter/receiver 306. The transmitter/receiver 306 can communicate with or provide wired or wireless communication between the microprocessor 304, the pump 310, and/or external devices, such as mobile or smart phones, tablets, or computers. The power supply 308 can supply energy to components of the delivery vessel.

The pump 310 can force or release a fixed amount of a therapeutic substance into the oral cavity through a connecting tube. Pump includes any apparatus that controls the release of a therapeutic agent. In some embodiments of the invention, a therapeutic substance is formed by mixing two or more components, for example by admixing in a reservoir, facilitated by the microprocessor of a control unit.

In some embodiments of the invention a sensor includes a miniaturized pH sensor, such as one or more FET-based pH sensors. The FET-based pH sensors can be included individually or within an array.

Figure 4:
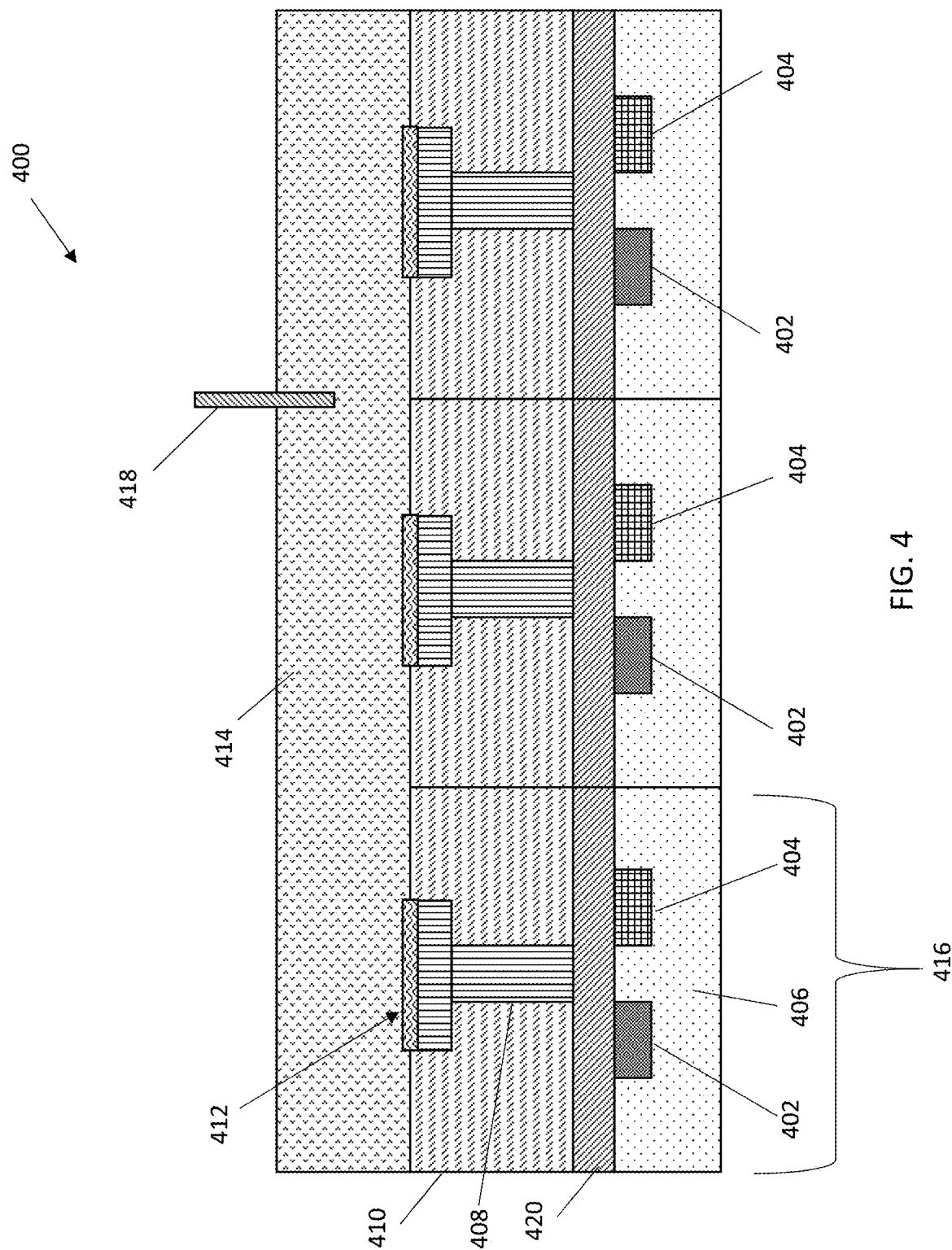
FIG. 4 depicts an exemplary system according to one or more embodiments of the present invention.

FIG. 4 illustrates an exemplary array of FET-based pH sensors 400 according to one or more embodiments of the present invention. The array 400 includes a plurality of FET-based pH sensors 416, which can each include a FET silicon substrate 406 and a source 402 and drain 404. FET Silicon substrate 406 can include silicon or doped silicon, for example the substrate 406 can include a silicon-on-insulator wafer (SOI) with lightly doped p-type silicon. The FET-pH sensor 416 can include an oxide layer 410. The FET-pH sensor 416 includes a gate dielectric 420 atop the FET silicon substrate 406. The FET-based pH sensor array 400 includes a reference electrode 418. The reference electrode 418 can include, for example, silver chloride. The reference electrode 418 A gate 408, including a pH sensing surface 412, can be embedded within or on top of the oxide layer 410.

Each of the pH sensing surface 412 and the reference electrode 418 can have surfaces externally accessible to the FET-based pH sensor 416 such that they can be placed into contact with oral cavity fluids, such as saliva 414, in the oral cavity of a patient. FIG. 4 depicts an embodiment in which saliva 414 is placed in contact with the pH sensing surface 412 and reference electrode 418.

Source 402, and drain 404 can be composed of materials conventionally used for such components in FET-devices and can be formed by conventional methods. Source 402 and drain 404 are formed on opposing sides of the gate 608. For example, source 402 and drain 404 can be formed with an epitaxial growth process to deposit a crystalline layer onto the FET substrate 406. The epitaxial silicon, silicon germanium, and/or carbon doped silicon (Si:C) can be doped during deposition by adding a dopant or impurity to form a silicide. The epitaxial source/drain can be doped with an n-type dopant or a p-type dopant, which depends on the type of transistor. In some embodiments of the invention, the source 402 and drain 404 include heavily boron doped source and drain regions. Alternatively, the source/drain 402/404 can be formed by incorporating dopants into the substrate 406.

Oxide layer 410 can be formed over the source 402 and drain 404 and gate dielectric 420 and around the gate 408. The oxide layer 410 can include, for example, a low-k dielectric oxide. In some embodiments of the invention, oxide layer 410 includes tetra-ethyl orthosilicate (TEOS) oxide.

Gate 408 and pH sensing surface 412 can be the same material or different materials and can include any insulating material that is sensitive to pH. In some embodiments of the invention gate 408 and pH sensing surface 412 are the same material. The pH sensing surface 412 includes a pH sensitive material. In some embodiments of the invention, gate and/or pH sensing surface include hafnium dioxide ($HfO_2$), aluminum oxide ($Al_2O_3$), vanadium oxide ($V_2O_5$), titanium oxide ($TiO_2$), tungsten oxides, titanium nitride (TiN) or combinations thereof. In some embodiments of the invention, the pH sensing surface 412 (the external surface of the gate) determines a local pH of saliva. In some embodiments of the invention, pH sensing surface 412 is composed of $HfO_2$ or TiN.

The pH sensing 412 surface can have any shape. The sensing surface can have a length or diameter of about 5 to about 15 micrometers (μm), for example from about 5 to about 10 μm or from about 5 to about 8 μm.

Sensing of pH with a FET-based pH sensor can be performed in accordance with known methods. In operation, according to some embodiments of the invention, the sensing signal is a drain current $I_D$. Measurements can be made, for example, by setting the reference electrode voltage equal to a gate voltage, setting the drain to a small voltage (e.g., |25 mV|) and setting the source voltage to 0 V. The silicon substrate can be set to 0 V at the back side. A device including a FET-based pH sensor can be applied to a solution, including to saliva or a reference or standardized solution for example, such that a sensing surface and reference electrode are exposed to the fluid. Measurements of drain current can be taken and used to determine local pH.

In some embodiments of the invention, an apparatus including a FET-based pH sensor can be calibrated to determine sensing signal dependence on voltage and pH. After calibration, drain current can be measured at a fixed voltage and pH calculated therefrom.

Figure 5:
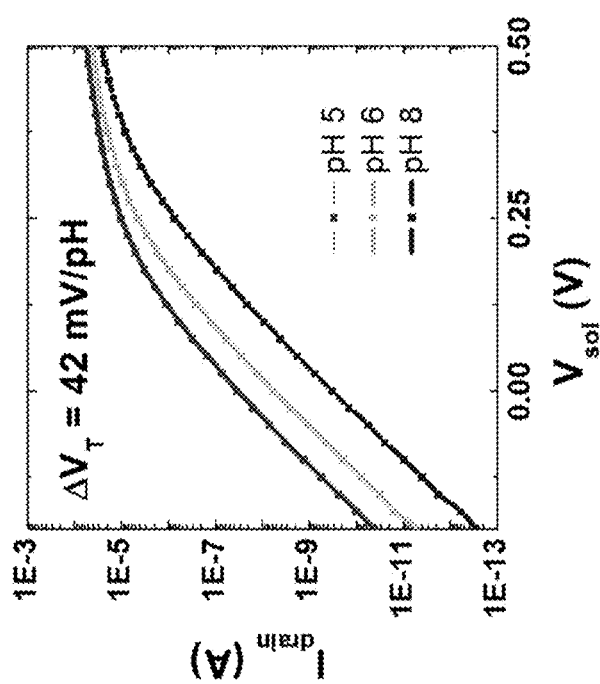
FIG. 5 is a chart depicting solution voltage versus drain current for an exemplary system according to one or more embodiments of the present invention.

FIG. 5 is a chart depicting drain current ($I_D$) versus gate voltage $V_{SOL}$ of an exemplary FET-based pH sensor for use in embodiments of the present invention. FIG. 5 demonstrates sensing signal ($I_D$) dependence on gate voltage and pH. Buffered solutions, such as phosphate buffer of 100 mM concentration, having known pH values of 5, 6, and 8 can each be applied to a FET-based pH sensor, such as a FET-based pH sensor for use in embodiments of the present invention. $I_D$ can be measured and plotted against the gate voltage $V_{SOL}$. FIG. 5 illustrates a FET-based pH sensor with a voltage per pH unit of 42 mV.

In some embodiments of the invention, calibration results are used to determine a pH of the oral cavity. For example, a fixed applied voltage can be applied to a system having one or more FET-based pH sensors or an array of FET-based pH sensors and a sensing signal ($I_D$) can be measured in real-time. From the sensing signal, pH can readily be calculated with the calibration results.

In some embodiments of the invention an intra-oral delivery system includes one or more BJT-based pH sensors. The BJT-based pH sensors can be included individually or within an array.

Figure 6:
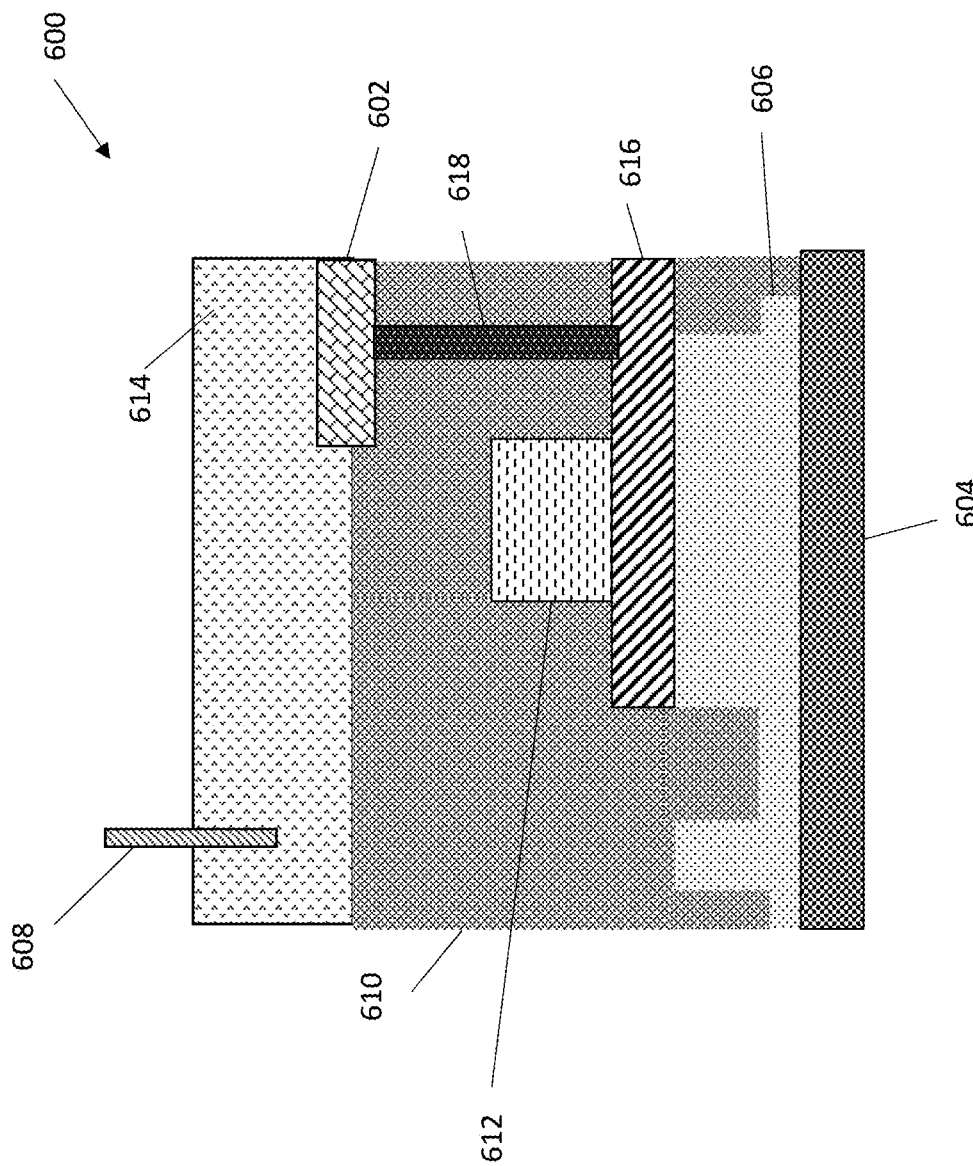
FIG. 6 depicts an exemplary system according to one or more embodiments of the present invention.

FIG. 6 illustrates an exemplary BJT-based pH sensor 600 for use in an intra-oral delivery system according to one or more embodiments of the present invention. BJT-pH sensor 600 includes a silicon substrate 604 and a collector 606 positioned on the silicon substrate 604. The BJT-pH sensor 600 also includes a base 616 formed on the collector 606. An emitter 612 can be formed on the base 616.

The BJT-pH sensor 600 can be an NPN type BJT or a PNP type BJT device. The selection of materials and dopant polarity can vary depending on whether the BJT-pH sensor is an NPN type or PNP type. For example, an NPN BJT can include a heavily doped n-type emitter 616, a p-type doped base 616, and a p-type doped collector 606. In some embodiments of the invention, the BJT-pH sensor 600 is a PNP type including, for instance, a heavily doped p-type emitter 616, an n-type doped base 616, and an n-type doped collector 606.

Silicon substrate 604 can include silicon or doped silicon. For example, the substrate 604 can include undoped silicon, p-type doped silicon or n-type doped silicon.

Collector 606 can include, for example, silicon, including doped or heavily doped silicon (i.e., more heavily doped than the substrate 604, which can be doped or undoped). The dopant polarity can be opposite to that of the substrate 604. For example, if the substrate 604 includes p-type doped silicon, the collector can include n-type heavily doped silicon. In some embodiments of the invention, collector 406 includes n-type heavily doped gallium arsenide (GaAs).

A base 616 can be formed on the collector 606. Base 616 can include, for instance, a doped silicon, such as silicon germanium (SiGe). In some embodiments of the invention, the silicon germanium is doped, or heavily doped (i.e., more heavily doped than the substrate 604). The dopant polarity can be opposite to that of the collector 606. For example, if the collector 606 includes n-type doped or heavily doped silicon, the base 616 can include p-type doped or heavily doped silicon germanium.

An emitter 612 can be formed on the base 616 and can include, for instance, silicon, polysilicon, or gallium arsenide. Emitter 612 can include polysilicon that is very heavily doped (i.e., doped more heavily than the collector 606 or the base 616).

As is further illustrated in FIG. 6, in one or more embodiments of the present invention BJT-pH sensor 600 includes a reference electrode 608 and a sensing surface 602. The reference electrode 608 can include, for example, a silver chloride reference electrode. The sensing surface 602 and reference electrode 608 can have surfaces externally accessible to the BJT-pH sensor such that they can be placed into contact with fluid, such as saliva 614 or saline or buffered solution. In some embodiments of the invention, the sensing surface(s) 602 are accessible to saliva when the BJT-pH sensor is included within an intra-oral delivery system according to one or more embodiments of the present invention. Base 616 can be electrically connected to the sensing surface 602 via a metal line 618. Metal line 618 can be a conductive metal wire, such as a tungsten wire.

The sensing surface 602 is positioned on or embedded within an oxide layer 610. The sensing surface 602 and reference electrode 608 each have an accessible surface for pH measurement of fluids in an oral cavity. Oxide layer 610 can be composed of any oxide-based dielectric or insulating material that can be used for insulation in semiconductor devices, including but not limited to silicon dioxide, aluminum oxide, hafnium oxide, and combinations thereof.

The sensing surface 602 can have any shape, including for instance a needle shape. The sensing surface 408 can have a length or diameter of about 5 to about 15 μm, for example from about 5 to about 10 μm or from about 5 to about 8 μm. The sensing surface 602 can be planar or have a three-dimensional shape.

In some embodiments of the invention, the sensing surface 602 includes conducting titanium nitride (TiN). The sensing surface 602 can be composed of any pH sensitive conducting material. In some embodiments of the invention, for example, sensing surface 602 includes a TiN film sputter deposited over a metal line 618. The sensing surface 602 can include, in some embodiments of the invention, platinum, ruthenium oxide, iridium oxide, conductive carbon, or combinations thereof.

In some embodiments of the present invention, an intra-oral delivery system includes a plurality of BJT-based pH sensors, wherein each BJT-based pH sensor includes one sensing surface. In some embodiments of the invention, a surgical apparatus includes a BJT-based pH sensor array.

Figure 7:
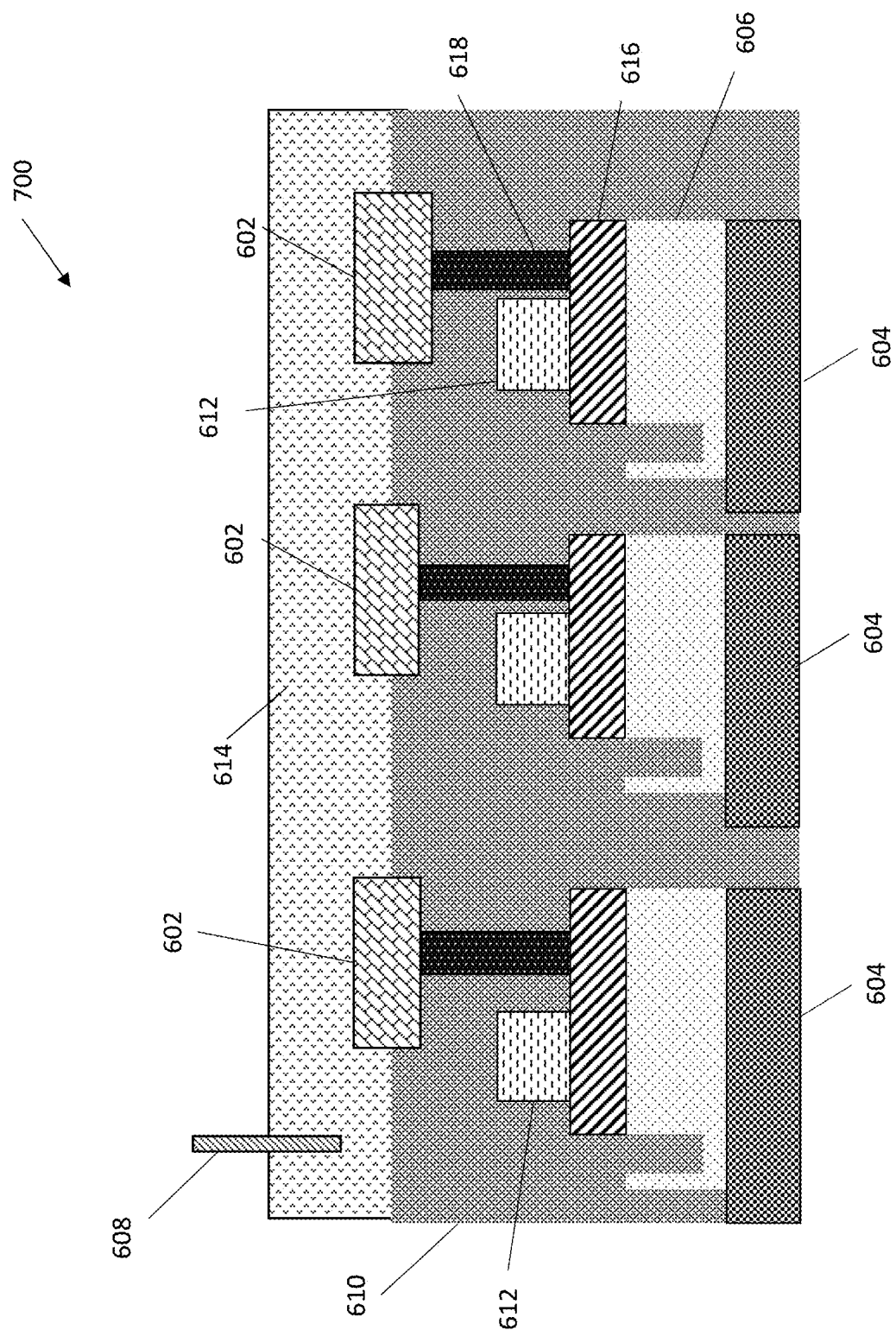
FIG. 7 depicts an exemplary system according to one or more embodiments of the present invention.

FIG. 7 depicts a cross-sectional side view of a portion of a pH sensor array 700 for use of sensing pH of fluids in an oral cavity according to one or more embodiments of the present invention. The array 700 includes a plurality of sensing surfaces 602. Each of the plurality of sensing surfaces can be connected to a metal line 618. The plurality of sensing surfaces 602 and metal lines 618 can be embedded within an oxide layer 610, such that the sensing surfaces 602 have a surface that can be accessible to a fluid, such as saliva in an intra-oral delivery system. The array 700 includes a reference electrode 608. In some embodiments of the invention, the array 700 includes one reference electrode 608. In some embodiments of the invention, not shown in FIG. 7, the array 700 includes a plurality of reference electrodes 608.

The pH sensor array 700 can include other components, such as each of the components that are included in a BJT-pH sensor 600 according to one or more embodiments of the invention. For example, the plurality of sensing surfaces 602 can each be electrically connected to one or more bases 616 via the plurality of metal lines 618. In some embodiments of the invention, each base 616 is positioned on a collector 606, which is positioned on a substrate 604. In some embodiments of the invention, a pH sensing array 700 includes a plurality of emitters 612.

In some embodiments of the invention, an intra-oral delivery system is placed entirely within a mouth. For example, in some embodiments of the invention, a miniaturized device including a pH sensor, a pump, a microprocessor, and a transmitter is coupled to the internal oral cavity, such as to the inner wall of a cheek or to a tooth, to monitor the pH of an oral cavity and, optionally, other substrates in the oral cavity over time.

In operation, in some embodiments of the invention, a pH sensing surface and reference electrode, such as a sensing surface of a BJT-based pH sensor or a FET-based pH sensor, can be brought into contact with saliva in an oral cavity of a patient. A pH can be determined in real-time and transmitted, via a wired connection or wirelessly, to a control unit 208 for a determination of whether and when to deliver a therapeutic agent or substance to the oral cavity.

Figure 8:
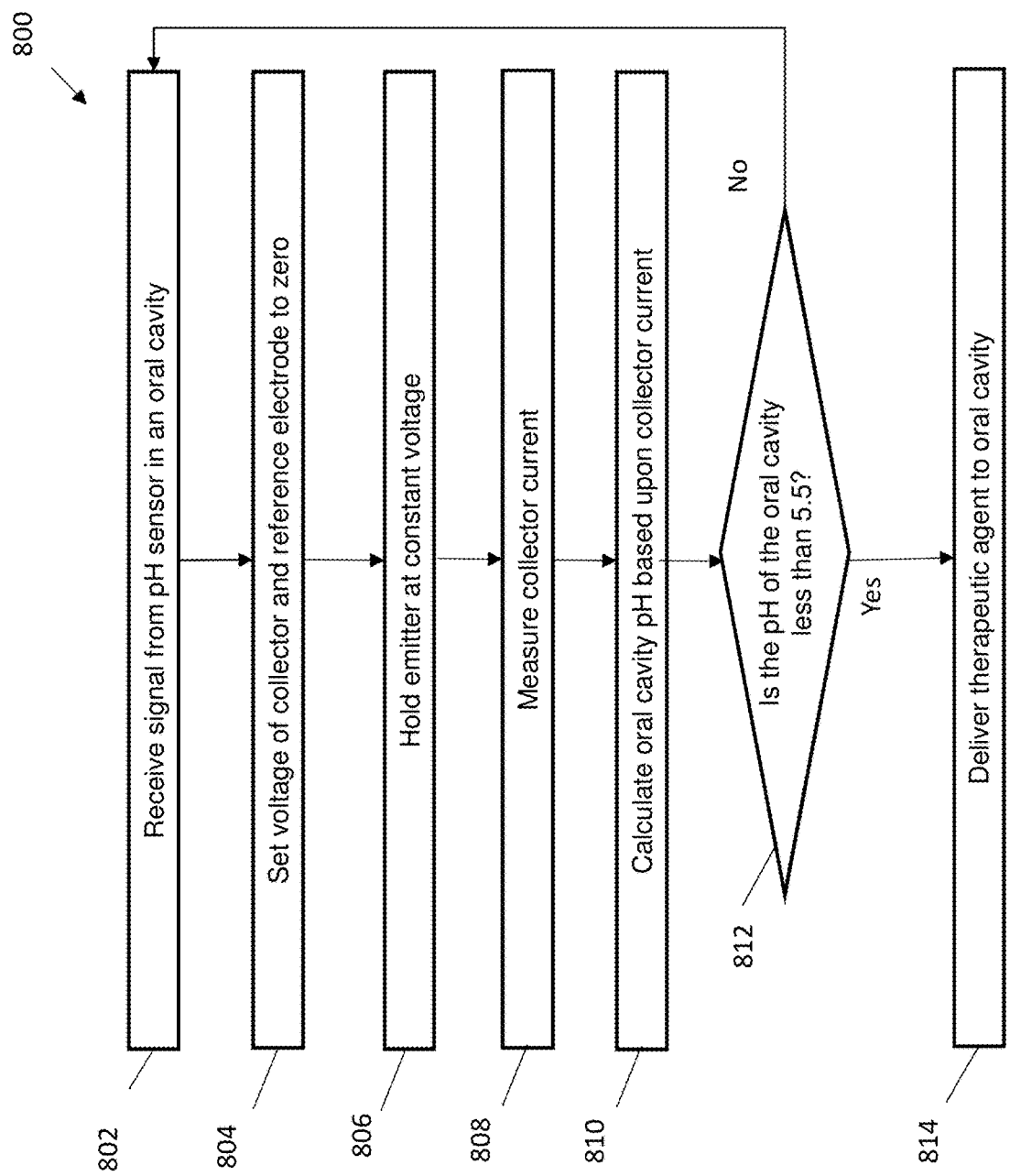
FIG. 8 depicts a flow diagram of an exemplary method according to one or more embodiments of the present invention.

FIG. 8 depicts a flow diagram for an exemplary method 800 of treating an oral condition according to one or more embodiments of the present invention. The method 800 includes, as shown at block 802, receiving a signal from a pH sensor in an oral cavity. The method 800 also includes, as shown at block 804, setting a voltage of a collector and reference electrode to zero. The method 800 also includes, as shown at block 806, holding an emitter at a constant voltage. The method 800 also includes, as shown at block 808, measuring a collector current. The method 800 also includes, as shown at decision block 812, determining whether the pH of the oral cavity is less than 5.5. Responsive to a determination that the pH is not less than 5.5, the method can return to block 802. Responsive to a determination that the pH is less than 5.5, the method can deliver a therapeutic agent to the oral cavity.

Figure 9:
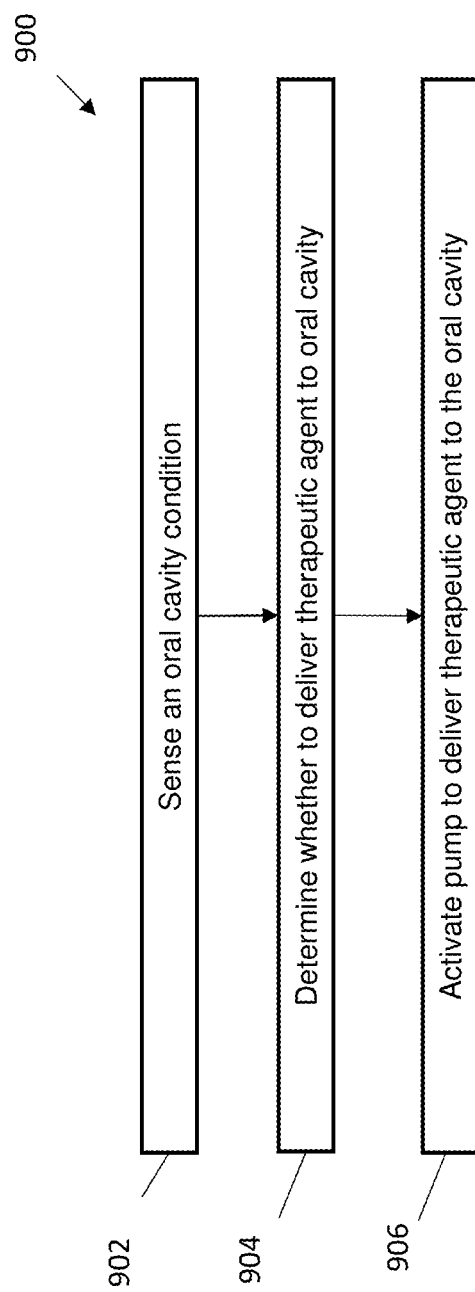
FIG. 9 depicts a flow diagram of an exemplary method according to one or more embodiments of the present invention.

FIG. 9 depicts a flow diagram of an exemplary method 900 for maintaining oral cavity health. The method 900 can include sensing, by a sensor positioned within the oral cavity of a patient, an oral cavity condition as shown at block 902. The method 900 can also include determining, by a control unit in communication with the sensor and a pump, whether to deliver a therapeutic agent to the oral cavity as shown at block 904. The method 900 can also include activating, by the control unit, the pump to deliver the therapeutic agent to the oral cavity as shown at block 906.

Figure 10:
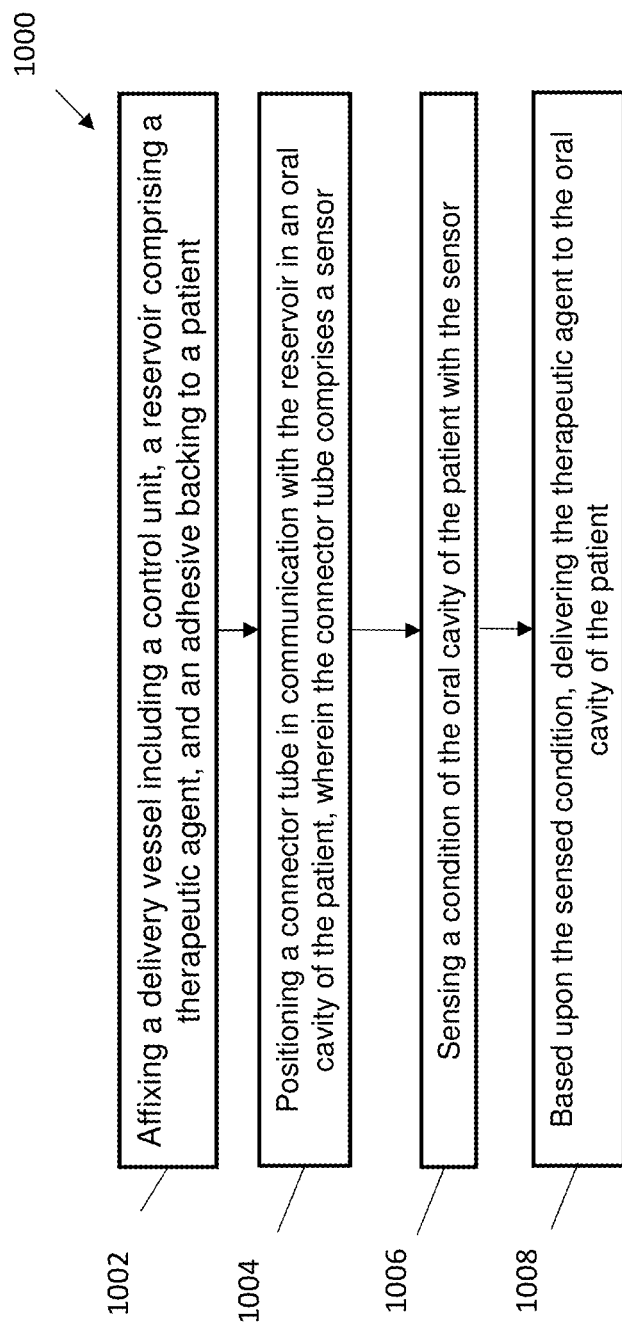
FIG. 10 depicts a flow diagram of an exemplary method according to one or more embodiments of the present invention.

FIG. 10 depicts a flow diagram of an exemplary method for intra-oral therapeutic delivery according to some embodiments of the present invention. The method 1000 includes, as shown at block 1102, affixing a delivery vessel including a control unit, a reservoir including a therapeutic agent, and an adhesive backing to a patient. The method 1000 can also include, as shown at block 1104, positioning a connector tube in communication with the reservoir in an oral cavity of the patient, wherein the connector tube includes a sensor. The method 1000 can also include as shown at block 1106, sensing a condition of the oral cavity of the patient with the sensor. The method 1000 can also include, as shown at block 1008, based upon the sensed condition, delivering the therapeutic agent to the oral cavity of the patient.

Embodiments of the present invention can provide a number of technical features and benefits. For example, embodiments of the present invention can provide improved oral health by preventing cavities, gingivitis, oral infection, halitosis, and the like. Embodiments of the invention can also deliver therapeutic agents to the oral cavity of a person in need thereof in an automated system, with minimal human intervention. Embodiments of the invention can provide automated delivery of oral therapeutic agents to individuals that are asleep or otherwise incapacitated without the need for continuous medical professional interaction and can provide administration of therapeutic agents outside of medical facilities, such as in a patient's home.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention the practical application or technical improvement over technologies found in the marketplace, or to enable others of ordinary skill in the art to understand the embodiments described herein.

What is claimed is:

1. A method for maintaining oral cavity health, the method comprising:
   providing a delivery vessel comprising a control unit and three or more reservoirs, wherein a first reservoir is filled with a therapeutic agent, a second reservoir is filled with a solvent, and a third reservoir is filled with a breath freshener;
   sensing, by a pH sensor positioned within the oral cavity of a patient, an oral cavity condition;
   comparing, by a control unit positioned on an external surface of the patient, the control unit in communication with the sensor and a pump, a measured pH from the pH sensor to a predetermined threshold; and
   activating, responsive to a determination that the measured pH is less than the predetermined threshold, the pump to deliver the therapeutic agent to the oral cavity after admixing the therapeutic agent with the solvent;

wherein the therapeutic agent comprises one or more of sodium bicarbonate, fluoride, chlorhexidine, artificial saliva, a topical antifungal agent, a topical cholinergic, or an anticholinergic agent.

2. The method of claim 1, wherein the oral cavity condition comprises intra-oral pH.

3. The method of claim 1, wherein the oral cavity condition comprises intra-oral humidity.

4. The method of claim 1, wherein the control unit is coupled to the patient.

5. The method of claim 4, wherein the control unit is coupled to a cheek of the patient.

6. The method of claim 4, wherein the control unit is coupled to a surface in the oral cavity of the patient.

7. A method for intra-oral therapeutic delivery, comprising:

affixing a delivery vessel comprising a control unit, three or more reservoirs, and an adhesive backing to an external surface of a patient, wherein a first reservoir is filled with a therapeutic agent, a second reservoir is filled with a solvent, and a third reservoir is filled with a breath freshener;

positioning a connector tube in communication with the reservoirs in an oral cavity of the patient, wherein the connector tube comprises a sensor;

sensing a pH condition of the oral cavity of the patient with the sensor;

comparing, by the control unit, the pH condition to a predetermined threshold; and based upon the sensed pH condition being less than the predetermined threshold, delivering the therapeutic agent to the oral cavity of the patient after admixing the therapeutic agent with the solvent;

wherein the therapeutic agent comprises one or more of sodium bicarbonate, fluoride, chlorhexidine, artificial saliva, a topical antifungal agent, a topical cholinergic, or an anticholinergic agent.

* * * * *